United States Patent
Zhang et al.

(10) Patent No.: US 10,215,876 B2
(45) Date of Patent: Feb. 26, 2019

(54) CATION EXCHANGE CAPACITY AND WATER SATURATION FROM ARRAY INDUCTION DATA

(71) Applicants: SCHLUMBERGER TECHNOLOGY CORPORATION, Sugar Land, TX (US); Saudi Aramco Oil Company, Dhahran (SA)

(72) Inventors: Ping Zhang, Albany, CA (US); Wael Abdallah, Al-Khobar (SA); Shouxiang Ma, Dhahran (SA)

(73) Assignees: SAUDI ARABIAN OIL COMPANY, Dhahran (SA); SCHLUMBERGER TECHNOLOGY CORPORATION, Sugar Land, TX (US)

( * ) Notice: Subject to any disclaimer, the term of this patent is extended or adjusted under 35 U.S.C. 154(b) by 20 days.

(21) Appl. No.: 15/286,776

(22) Filed: Oct. 6, 2016

(65) Prior Publication Data
US 2018/0100942 A1    Apr. 12, 2018

(51) Int. Cl.
*G01V 3/10* (2006.01)
*G01N 33/24* (2006.01)
*G01V 3/28* (2006.01)

(52) U.S. Cl.
CPC .............. *G01V 3/10* (2013.01); *G01N 33/24* (2013.01); *G01V 3/28* (2013.01)

(58) Field of Classification Search
CPC  G01R 19/0092; G01R 19/0084; G01R 21/06; G01R 19/00; G01R 15/181; G01R 31/40; G01R 27/06

USPC .............................. 324/123, 76.11, 107, 127
See application file for complete search history.

(56) References Cited

U.S. PATENT DOCUMENTS

| | | | | |
|---|---|---|---|---|
| 4,525,715 | A * | 6/1985 | Smith | ................... E21B 47/122 175/50 |
| 7,755,361 | B2 * | 7/2010 | Seydoux | .................. G01V 3/28 324/333 |
| 8,049,508 | B2 * | 11/2011 | Gorek | ...................... G01V 3/28 324/338 |
| 2003/0105590 | A1 | 6/2003 | Mollison et al. | |
| 2006/0042369 | A1 | 3/2006 | Al-Ruwaili | |
| 2006/0136135 | A1 | 6/2006 | Little et al. | |
| 2007/0061082 | A1 | 3/2007 | Seleznev et al. | |
| 2013/0248251 | A1* | 9/2013 | Kulkarni | ................. E21B 21/06 175/50 |

(Continued)

OTHER PUBLICATIONS

Archie, G. E., "The Electrical Resistivity Log as an Aid in Determining Some Reservoir Characteristics", Transactions of the AIME, 1942, 146(1), pp. 54-62.

(Continued)

*Primary Examiner* — Giovanni Astacio-Oquendo
(74) *Attorney, Agent, or Firm* — Bridget Laffey

(57) ABSTRACT

In-phase and quadrature components have different relationships with some important petrophyscial parameters, such as water saturation and mineral cation exchange capacity (CEC). In clay-containing subterranean rock formation such as shaly sand formations, these parameters can be estimated using different components of array induction tool data combined with other knowledge about the clay-containing formation. Some parameters, such as mobility and fraction of counterions are valid in cases where the pore water solution is an electrolyte of NaCl.

12 Claims, 2 Drawing Sheets

(56) References Cited

U.S. PATENT DOCUMENTS

| | | | |
|---|---|---|---|
| 2016/0097876 A1* | 4/2016 | Freed | G01V 3/24 |
| | | | 703/2 |
| 2016/0362971 A1* | 12/2016 | Benson | E21B 7/06 |
| 2017/0075021 A1* | 3/2017 | Thiel | G01V 3/38 |
| 2017/0122099 A1* | 5/2017 | Yao | E21B 49/003 |
| 2017/0199298 A1* | 7/2017 | Hu | G01V 5/12 |

OTHER PUBLICATIONS

Clavier, C. et al., "Theoretical and Experimental Bases for the Dual-Water Model for Interpretation of Shaly Sands", SPE 6859, Society of Petroleum Engineers Journal, 1984, 24(2), 16 pages.

Devarajan, S. et al., "Pore-Scale Analysis of the Waxman-Smits Shaly Sand Conductivity Model", presented at the SPWLA Annual Logging Symposium, Vera Cruz, Mexico, 2006, 9 pages.

Hill, H. J. et al., "Bound Water in Shaly Sands—Its Relation to Qv and Other Formation Properties", The Log Analyst, 1979, 20(3), pp. 3-19.

Huff, G. F., "A Correction for the Effect of Comminution on the Cation Exchange Capacity of Clay-Poor Sandstones", SPE-14877, SPE Formation Evaluation, 1987, 2(3), pp. 338-344.

Leroy, P. et al., "A triple layer model of the surface electrochemical properties of clay minerals", Journal of Colloid and Interface Science, 2004, 270, pp. 371-380.

Ma, S. M., et al., "Cased-Hole Reservoir Saturation Monitoring in Mixed-Salinity Environments—A New Integrated Approach," SPE 92426, presented at the SPE Middle East Oil and Gas Show and Conference, Kingdom of Bahrain, 2005, 10 pages.

Ma, S. M. et al., "Resolving the Mixed Salinity Challenges with a Methodology Developed from Pulsed Neutron Capture Gamma Ray Spectral Measurements," SPE 170608, presented at the SPE Annual Technical Conference and Exhibition, Amsterdam, The Netherlands, 2014, 12 pages.

McCoy, D. D. et al., "Water-Salinity Variations in the Ivishak and Sag River Reservoirs at Prudhoe Bay", SPE-28577, SPE Reservoir Engineering, 1997, 12(1), pp. 37-44.

Meier, L. P. et al., "Determination of the cation exchange capacity (CEC) of clay minerals using the complexes of copper (II) ion with triethylenetetramine and tetraethylenepentamine", Clays and Clay Minerals, 1999, 47(3), pp. 386-388.

Rathmell, J. J. et al., "Application of Low Invasion Coring and Outcrop Studies to Reservoir Development Planning for the Villano Field", SPE-53718, presented at the Sixth Latin American and Caribbean Petroleum Engineering Conference, Caracas, Venezuela, 1999, 12 pages.

Rathmell, J. J. et al., "Low Invasion, Synthetic Oil-Base Mud Coring in the Yacheng 13-1 Gas Reservoir for Gas-in-Place Calculation", SPE-29985, presented at the International Meeting on Petroleum Engineering, Beijing, China, 1995, 12 pages.

Revil, A., "Spectral induced polarization of shaly sands: Influence of the electrical double layer", WO2517, Water Resources Research, 2012, 48, 23 pages.

Waxman, M. H. et al., "Electrical Conductivities in Oil-Bearing Shaly Sands", SPE-1863, Society of Petroleum Engineers Journal, 1968, 8(2), pp. 107-122.

Zhang, J-h. et al., "Estimation of True Formation Resistivity and Water Saturation with Time-Lapse Induction Logging Method", The Log Analyst, 1999, 40(2), pp. 138-148.

Search Report and Written Opinion of Related International Patent Application No. PCT/US2017/055217, dated Jan. 16, 2018, 11 pages.

* cited by examiner

CATION EXCHANGE CAPACITY AND WATER SATURATION FROM ARRAY INDUCTION DATA

FIELD

The subject disclosure generally relates to the field of evaluating reservoirs in the oil and gas industry. More particularly, the subject disclosure relates to using induction tool measurement data to calculate formation rock cation exchange capacity and formation water saturation.

BACKGROUND

For log interpretation for shaly sand reservoirs, there are several models available. Commonly used models include the Waxman and Smits (W-S), 1968 model, and dual water (D-W) model of Clavier et al., 1984. See, Waxman and Smits, Electrical conductivities in oil-bearing shaly sands, SPEJ 8(2), 107-122, (1968); and Clavier, et al, The theoretical and experimental bases for the dual water model for the interpretation of shaly sands, SPE 6859, 1977 ATCE, SPEJ April (1984). Although these models have successes in the interpretation of electric-log responses of shaly sand homogeneous reservoir rocks, the models are not explicit in their predictions of electrical conductivity with respect to rock structure, spatial fluid distribution in the pore space, wettability, or clay mineral distribution. See, Devarajan, S., Toumelin, E., Torres-Verdín, C., Thomas, E. C., "Pore-scale analysis of the Waxman-Smits shaly sand conductivity model", SPWLA, Jun. 4-7 (2006). The models rely on information about clay cation exchange capacity (CEC) and formation water salinity ($R_w$) as demonstrated infra.

Archie, G. E., the Electrical Resistivity Log as an Aid in Determining Some Reservoir Characteristics, Trans. of AIME 146 (1), (1942) discusses the fundamental empirical correlation for interpreting conductivity measurements:

$$\sigma^T = \varphi^m S_w^n \sigma^w$$

Where $\sigma^T$ is formation true resistivity, $\sigma^w$ is formation water resistivity, $S_w$ is water saturation, n is saturation exponent, $\varphi$ is reservoir total porosity, and m is cementation exponent.

When clay minerals are present, Waxman-Smits empirical model can be applied and it is characterized by the following equation:

$$\sigma^t = \varphi^m S_w^n \left( \sigma_w + \frac{BQ_v}{S_w} \right)$$

Where, m* and n* are Archie cementation and saturation exponents for shaly sands applied to total pore volume. B is specific cation conductance in $(ohm^{-1})/(meq/ml)$, Qv is the cation exchange capacity (CEC) per unit pore volume:

$$Q_v = \rho_g CEC \frac{1-\varphi}{\varphi}$$

Where CEC is in meq/gram of dry rock, $\rho_g$ is rock grain density in g/cc, and $\varphi$ is total porosity. In clean zones (no clay), CEC=0, thus Qv=0, m*=m, n*=n, and the W-S model becomes Archie model.

The D-W model has been developed based on the double layer effect close to the grain surface, the D-W equation:

$$\sigma^t = \varphi^{m_0} S_w^{n_0} \left[ \sigma_{wF} + \frac{S_{wB}}{S_w}(\sigma_{wB} + \sigma_{wF}) \right]$$

Where $\sigma_{wB}$ is clay bound water resistivity, $\sigma_{wF}$ is free formation water resistivity, SwB is clay bound water saturation with respect to total pore volume, and can be estimated using the HSK model proposed by Hill, H. J., Shirley, O. J., and Klein, G. E, Bound Water in Shaly Sands—Its Relation to Qv and Other Formation Properties. The Log Analyst 20 (3): 3 (1979):

$$S_{wB} = Q_v \left( \frac{a_1}{\sqrt{C_{NaCl}}} + a_2 \right)$$

Where $a_1$ and $a_2$ are constants and $C_{NaCl}$ is NaCl concentration in equivalent/liter. In clean zones (no clay), $S_{wB}$=0, $m_0$=m, $n_0$=n, the D-W model becomes the Archie model.

CEC is measured in the laboratory by potentiometric titration methods. See, Meier, L. P., and G. Kahr, Determination of the cation exchange capacity (CEC) of clay minerals using the complexes of copper (II) ion with triethylenetetramine and tetraethylenepentamine, Clays Clay Miner, 47(3), 386-388 (1999). Uncertainties associated with this laboratory measurement are many, including how representative of the laboratory sample analyzed to downhole conditions (clays can be sensitive to environment changes) and details of the laboratory sample preparation and analysis such as the degree to which the clay mineral geometry is altered by the disaggregation of the core sample, which can be enhanced by grinding to grain size particles. See, Huff, G. F., A Correction for the Effect of Comminution on the Cation Exchange Capacity of Clay-Poor Sandstones, SPE Form Eval 2 (3): 338-344, SPE-14877 (1987).

Formation water salinity or formation water resistivity $R_w$ can be obtained by water analysis in laboratory. See, Ma, S., Hajari, A., Berberian, G. & Ramamoorthy, R: "Cased-Hole Reservoir Saturation Monitoring in Mixed Salinity Environments—A New Integrated Approach," SPE 92426 MOES (2005). Without a robust continuous in-situ measurement, formation water salinity is often assumed to be constant within the hydrocarbon column, and usually there is little data regarding $R_w$ other than from formation sampling. In several cases in which the $R_w$ distribution has been studied in depth, it was found to vary in systematic ways within the hydrocarbon column. See, McCoy, D. and Fisher, T. E., Water-Salinity Variations in the Ivishak and Sag River Reservoirs at Prudhoe Bay, SPE Res Eng 12 (1): 37-44, SPE-28577 (1997); Rathmell, J. J., Bloys, J. B., Bulling, T. P. et al., Low Invasion, Synthetic Oil-Base Mud Coring in the Yacheng 13-1 Gas Reservoir for Gas-in-Place Calculation, Presented at the International Meeting on Petroleum Engineering, Beijing, China, 14-17 November SPE-29985 (1995); and Rathmell, J., Atkins, L. K., and Kralik, J. G., Application of Low Invasion Coring and Outcrop Studies to Reservoir Development Planning for the Villano Field, Presented at the Latin American and Caribbean Petroleum Engineering Conference, Caracas, Venezuela, 21-23 April, SPE-53718 (1999).

Efforts have been made recently to derive this salinity information from special wireline logs. See, Ma, S., Pfutzer, H., Hajari, A., Musharfi, N., Saldungaray, P. & Azam, H: "Resolving Mixed Salinity Challenge with a Methodology Developed from Pulsed Neutron Capture Gamma Ray Spectral Measurements," SPE 170608, SPE ATCE, Amsterdam, Oct. 27-29 (2014).

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

According to some embodiments, a method of estimating parameters for a clay-containing subterranean rock formation is described. The method includes: positioning a tool in a borehole traversing the clay-containing formation, the tool comprising one or more transmitter coils and a plurality of receiver coils; inducing alternating current loops in the clay-containing formation using the one or more transmitter coils; measuring a signal resulting from the induced current loops using the receiver coils; and combining measurements from the receiver coils and knowledge about the clay-containing formation to obtain an estimate of water saturation in the formation. According to some embodiments, an estimate of cation exchange capacity (CEC) in the formation is also obtained by the combining.

The water saturation and CEC estimates can be obtained using a first relationship between real conductivity and a first plurality of formation parameters and a second relationship between complex conductivity and a second plurality of formation parameters. According to some embodiments, the first and second pluralities of formation parameters both include water saturation and CEC. The first plurality of formation parameters also can include: water conductivity, grain density; mobility of counterions; and/or an electric formation factor. The water conductivity can be calculated using water salinity, which can be estimated using borehole water samples. In some cases, the formation temperature and the grain density can be obtained from temperature and density and temperature log data. The second plurality of formation parameters can also include: grain density; a fraction of counterions in a Stern layer; and/or mobility of counterions within the Stern layer.

According to some embodiments, the knowledge about the formation is obtained from laboratory measurements and/or measurement logs. Examples of such measurement logs include a density and temperature logs from which temperature and grain density is obtained.

According to some embodiments the clay-containing subterranean rock formation is a shaly-sand formation. The tool can be suspended from a wireline, and the plurality of receiver coils can include at least three receiver coils arranged in a receiver array.

As used herein the terms "real" and "in-phase" are used interchangeably, and the terms "imaginary" and "quadrature" are used interchangeably.

Further features and advantages of the subject disclosure will become more readily apparent from the following detailed description when taken in conjunction with the accompanying drawings.

BRIEF DESCRIPTION OF THE DRAWINGS

The subject disclosure is further described in the detailed description which follows, in reference to the noted plurality of drawings by way of non-limiting examples of the subject disclosure, in which like reference numerals represent similar parts throughout the several views of the drawings, and wherein.

DETAILED DESCRIPTION

The particulars shown herein are by way of example and for purposes of illustrative discussion of the examples of the subject disclosure only and are presented in the cause of providing what is believed to be the most useful and readily understood description of the principles and conceptual aspects of the subject disclosure. In this regard, no attempt is made to show structural details in more detail than is necessary, the description taken with the drawings making apparent to those skilled in the art how the several forms of the subject disclosure may be embodied in practice. Furthermore, like reference numbers and designations in the various drawings indicate like elements.

It is desirable to have both CEC and $S_w$ measured downhole continuously across a shaly sand reservoir at reservoir conditions, and it is advantageous if these fundamental reservoir properties can be extracted from advanced processing of existing measurements such as the AIT log, which is very commonly available in formation evaluation wells.

Interfacial polarization phenomena has been widely observed among electromagnetic (EM) surveys. For a formation with clay inclusions, the interfacial polarization can have significant impacts on EM measurements. A resistivity interpretation method that neglects interfacial polarization effects will lead to inaccurate estimation of petrophysical properties of formations. Clay minerals have negligible bulk conductivity and possess surface charges that give rise to surface conductance. Electrical double layers, Stern layers and diffuse layers, are formed around clay particles and they tend to dictate interfacial polarization. Surface charges within Stern layers mostly contribute to interfacial polarization, while charges within diffuse layers and pore fluid control current conduction.

Complex conductivity has been used to more properly describe the conductive phenomena of the porous media containing clay minerals under external EM fields. Normally, in-phase (or real) and quadrature (or imaginary) components are used to denote a complex conductivity.

It has been found that the in-phase and quadrature components have different relationships with some important petrophyscial parameters such as water saturation and mineral cation exchange capacity (CEC). According to some embodiments, these parameters can be estimated using different components of induction logging data available in almost every well drilled. According to some embodiments, details of how to use in-phase and quadrature components of array induction data to estimate water saturation and CEC values are described.

Figure 1:
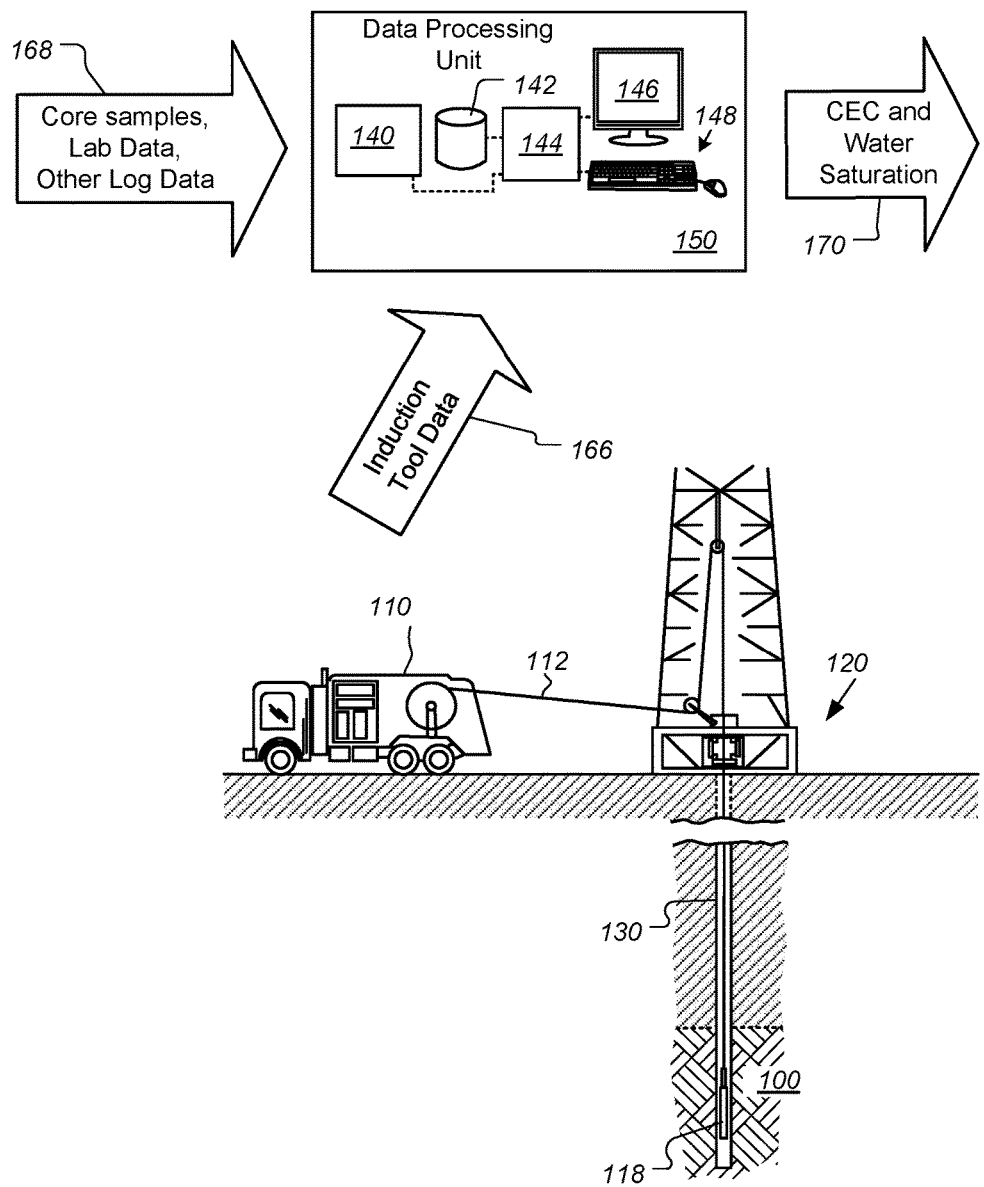
FIG. 1 is a diagram showing an induction tool being deployed in a first wellbore, along with a processing unit configured to estimate formation water saturation ($S_w$) and mineral cation exchange capacity (CEC), according to some embodiments.

FIG. 1 is a diagram showing an induction tool being deployed in a first wellbore along with a processing unit configured to estimate formation water saturation and mineral cation exchange capacity (CEC), according to some embodiments. Wireline truck 110 is deploying wireline cable 112 into first well 130 at wellsite 120. Induction tool 118 is disposed on the end of the cable 112 in a subterranean rock formation 100. According to some embodiments, formation 100 is a clay-containing reservoir formation such as a shaly sand formation. Induction tool 118, according to some embodiments, is an array induction tool such as Schlumberger's Array Induction Imager Tool. Data from the tool 118 from rock formation 100 are retrieved at the surface in logging truck 110. According to some embodiments, on separate logging procedures one or more other tools such as a density tool, a neutron porosity tool, and/or a sonic tool, none of which are shown for clarity, are run in well 130 using truck 110.

According to some embodiments, the induction tool data 166 is processed in a data processing unit 150, which can be located in the logging truck 110 or at some other location at wellsite 120. According to some embodiments, data processing unit 150 is located at one or more locations remote from the wellsite 120. The processing unit 150 includes one or more central processing units 144, storage system 142, communications and input/output modules 140, a user display 146 and a user input system 148. Data processing unit 150 can be used for carrying out the processing activity described herein. The spectroscopy data 166 is combined with other knowledge 168 about the reservoir 100. As will be described in further detail, infra, knowledge 168 can include, for example, information from core samples, other laboratory data, and data from other logs (such as density logs). By combining the induction tool data 166 with other knowledge 168, processing unit 150 can estimate values for CEC and water saturation for reservoir 100.

When the surface of a nonconductive mineral, such as clay minerals and silica grains, is exposed to electrolytes, it acquires charges due to ionic adsorption, protonation/deprotonation of the hydroxyl groups, and dissociation of other potentially active surface groups. See, Leroy, P., and A. Revil, a triple layer model of the surface electrochemical properties of clay minerals: Journal of Colloid and Interface Science, 270, 371-380. (2004). If external electromagnetic (EM) fields are applied to a formation, both electrical conduction, due to charge carries, and interfacial polarization, due to surface charges, co-exist. The measured EM fields are influenced by both effects. Electrical conduction describes the movement of the charge carries under the influence of the external EM fields. This well understood phenomena can be described by Ohm's law. The polarization of clay particles is largely due to charge accumulation and movements at host-inclusion interfaces. A common theory that describe this interfacial polarization is an electrical double layer. At the surface of the clay particles, both Stern and diffuse layers are formed due to charge adsorption and movement. In the presence of an externally applied electric field, the double layer develops a counter ion cloud and diffused-charge distribution around host-inclusion interfaces. Dynamics of accumulation/depletion of charge concentrations around host-inclusion interfaces influence the magnitude and phase of the EM response of a reservoir formation containing clay minerals.

The formation electrical property is described by complex conductivity:

$$\sigma = \sigma^R + \sigma^I \quad (1)$$

where $\sigma^R$ is the in-phase (real) component and $\sigma^I$ is the quadrature (imaginary) component of the total conductivity, respectively. For a porous media containing clay minerals, this total conductivity depends on conductivity of pore fluid, saturation, ion mobility and CEC of clay inclusions. In particular, the in-phase and quadrature components have different relationships with these parameters:

$$\sigma^R = \frac{S_w^n}{F}\left[\sigma_w + \frac{2m\beta_+ + \rho_g CEC}{3}(F-1)\right] \quad (2)$$

where $\sigma_w$ is formation water conductivity (which is inversely proportional to formation water resistivity $R_w$), $\rho_g$ is grain density, $\beta_+$ is mobility of the counterion in pore water solution, F is electric formation factor, $F = \phi^{m^*}$, $S_w$ is water saturation, $n^*$ is saturation exponent, $m^*$ is cementation exponent for shaly sand formation and CEC is cation exchange capacity; and $$\sigma^I = 2/3 \beta_+^s f \rho_g S_w^{n-1} CEC \quad (3)$$

where f is fraction of counterion in the Stern layer, $\beta_+^s$ is mobility of the counterion within Stern layer.

Among all the parameters related with in-phase and quadrature components of the formation conductivity, the water saturation and CEC are the key petrophysical parameters that can be used to calculate the oil reserve and to identify the clay types. It may seem difficult to estimate $S_w$ and CEC without detailed knowledge of the other parameters. However, in practical applications, if we consider typical clay minerals with pore water solution is an electrolyte of NaCl, most of the parameters have either well-defined values from laboratory experiments or they are within a narrow variation range. According to some embodiments, this enables us to estimate $S_w$ and CEC values using induction logs with following steps I and II.

I. Rewrite Equations (2) and (3) as:

$$\sigma^R = \frac{S_w^n}{F}\left[\sigma_w + \frac{Q\sigma^I}{KS_w^{n-1}}\right]; \text{ and} \quad (4)$$

$$CEC = \frac{\sigma^I}{KS_w^{n-1}} \quad (5)$$

where $K = \frac{2}{3}\beta_+^s f \rho_g$, and $Q = \frac{2}{3}m\beta_+\rho_g(F-1)$.

For typical clay minerals with pore water of an electrolyte of NaCl:

$$\beta_+^s(25° C., Na^+) = 1.5 \times 10^{-10} \text{ m}^2 \text{ s}^{-1} \text{ V}^{-1}$$

$$\beta_+(25° C., Na^+) = 5.2 \times 10^{-8} \text{ m}^2 \text{ s}^{-1} \text{ V}^{-1}$$

For most clay minerals, f is within a narrow range (0.85 to 0.95). A typical value is f=0.90. Density $\rho_g$ can be derived from laboratory density measurements. For typical clay mineral, $\rho_g \approx 2650$ kg m$^{-3}$. See, Revil, A., Spectral induced polarization of shaly sands: Influence of the electrical double layer: Water resources research, Vol 48, W02517 (2012). The saturation and cementation exponents $m^*$ and $n^*$ are typically assigned to 2 for most petrophysical calculations (in water wet homogeneous formations), actual values usually obtained through core laboratory measurements. The formation factor F can be acquired through many traditional logs, such as a resistivity log across a water leg (F=$\sigma_w/\sigma_o$, where $\sigma_o$ is formation conductivity in the water leg) or density and neutron logs (F=$1/\phi^{m^*}$). Temperature T, can be also be obtained from logs. For water conductivity, downhole sampling is commonly used to determine water salinity $C_w$ and therefore water conductivity can be calculated as:

$$\sigma_w = \frac{C_w^{0.955}}{A(0.0123C_w^{0.955} + 3647.5)}$$

$$\text{where,} \quad A = \frac{82}{1.8T + 39}.$$

See, Zhang, J., Hu, Q. and Liu, Z., Estimation of true formation resistivity and water saturation with time-lapse induction logging method, The log analysis, Vol. 40, No. 2, P. 138-148 (1999).

II. Both K and Q can be calculated using the parameters shown above. Then equations (4) and (5) will allow us to determine both water saturation and CEC.

Figure 2:
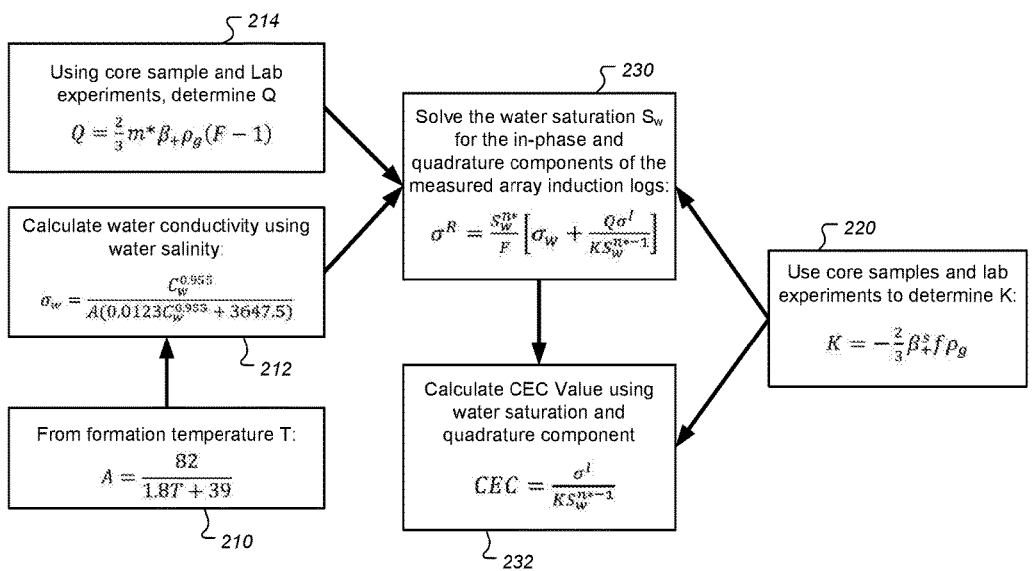
FIG. 2 is a block diagram illustrating aspects of estimating CEC and formation water saturation based on induction log data and other knowledge, according to some embodiments.

FIG. 2 is a block diagram illustrating aspects of estimating CEC and formation water saturation based on induction log data and other knowledge, according to some embodiments. In block 210, the value of a temperature correction factor "A" is calculated using formation temperature. According to some embodiments, formation temperature can be obtained from other logs, such as the temperature log data. In block 212 the water conductivity is calculated using water salinity and the value of A from block 210. Water salinity can be obtained, for example from downhole sampling. In block 214, the value of Q can be calculated, for example, using a core sample and lab experiments. In block 220, the value of K can be calculated, for example, using core samples and lab experiments. In blocks 230 and 232 the two equations are solved to yield to two remaining unknowns, CEC and water saturation.

Since the induction data are logged for almost all the production wells, the methodology described herein provides a practical and efficient way to estimate water saturation and CEC values, which are parameters used in formation evaluation, reservoir surveillance and reservoir management. Thus, according to some embodiments, if we consider typical clay minerals with pore water solution is an electrolyte of NaCl, then the described techniques can be used to estimate CEC (and thus clay typing for different clays have different CECs), and formation water saturation using measured array induction data.

Some of the methods and processes described above can be performed by a processor. The term "processor" should not be construed to limit the embodiments disclosed herein to any particular device type or system. The processor may include a computer system. The computer system may also include a computer processor (e.g., a microprocessor, microcontroller, digital signal processor, or general purpose computer) for executing any of the methods and processes described above.

The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

Some of the methods and processes described above, as listed above, can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

Although only a few examples have been described in detail above, those skilled in the art will readily appreciate that many modifications are possible in the examples without materially departing from this subject disclosure. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method of estimating parameters for a clay-containing subterranean rock formation comprising:
    positioning a tool in a borehole traversing the clay-containing formation, the tool comprising one or more transmitter coils and a plurality of receiver coils;
    inducing alternating current loops in the clay-containing formation using the one or more transmitter coils;
    measuring a signal resulting from the induced current loops using the receiver coils;
    combining measurements from the receiver coils and knowledge about the clay-containing formation to obtain an estimate of water saturation in the formation and an estimate of cation exchange capacity in the formation; and
    wherein the estimate of water saturation in the formation and the estimate of cation exchange capacity are obtained using a first relationship between real conductivity and a first plurality of formation parameters and a second relationship between complex conductivity and a second plurality of formation parameters.

2. The method of claim 1 wherein the first and second pluralities of formation parameters both comprise water saturation and the estimate of cation exchange capacity.

3. The method of claim 2 wherein the first plurality of formation parameters further comprises: water conductivity, grain density; mobility of counterions; and an electric formation factor.

4. The method of claim 3 wherein said water conductivity is calculated using water salinity and temperature.

5. The method of claim 4 wherein said water salinity is estimated using borehole water samples.

6. The method of claim 5 wherein said temperature and said grain density are obtained from temperature and laboratory density measurement data.

7. The method of claim 2 wherein the second plurality of formation parameters further comprises: grain density; a fraction of counterions in a Stern layer; and mobility of counterions within the Stern layer.

8. The method of claim 1 wherein said knowledge about the formation is obtained from laboratory measurements and/or measurement logs.

9. The method of claim 8 wherein said measurement logs include a laboratory density measurement and a temperature log from which temperature and grain density is obtained.

10. The method of claim 1 wherein the clay-containing subterranean rock formation is a shaly-sand formation.

11. The method of claim 1 wherein the tool is suspended from a wireline.

12. The method of claim 1 wherein said plurality of receiver coils comprises at least three receiver coils arranged in a receiver array.

* * * * *